United States Patent [19]
De Resende

[11] Patent Number: 5,400,779
[45] Date of Patent: Mar. 28, 1995

[54] CONTINUOUS-FLOW RESPIRATORY RESUSCITATION UNIT

[76] Inventor: Jefferson G. De Resende, SOS 103, Bloco C, Apt. 105, Asa Sul, 70342-Brasilia, DF, Brazil

[21] Appl. No.: 835,454

[22] Filed: Apr. 15, 1993

[30] Foreign Application Priority Data

Jun. 28, 1990 [BR] Brazil .................................. 9003095
Nov. 12, 1990 [BR] Brazil .................................. 9005807

[51] Int. Cl.⁶ ........................................... A61M 16/00
[52] U.S. Cl. .................. 128/205.24; 128/204.18; 128/207.12
[58] Field of Search ........... 28/203.14, 203.28, 203.29, 28/204.18, 204.21, 204.24, 204.25, 205.12, 205.13, 205.14, 205.15, 205.16, 205.17, 205.18, 205.24, 205.25, 207.14, 207.12

[56] References Cited

U.S. PATENT DOCUMENTS

| | | | |
|---|---|---|---|
| 2,918,917 | 12/1959 | Emerson | 128/205.24 X |
| 3,957,047 | 5/1976 | Freytag et al. | 128/204.24 |
| 4,502,481 | 3/1985 | Christian | 128/205.24 |
| 4,805,613 | 2/1989 | Bird | 128/204.25 |
| 5,301,667 | 4/1994 | McGrail et al. | 128/205.14 |

FOREIGN PATENT DOCUMENTS

| | | |
|---|---|---|
| 1449918 | 7/1965 | France . |
| 90720 | 4/1966 | France . |
| 2320118 | 3/1977 | France . |

*Primary Examiner*—Edgar S. Burr
*Assistant Examiner*—Eric P. Raciti
*Attorney, Agent, or Firm*—James Ray & Associates

[57] ABSTRACT

A continuous-flow respiratory resuscitation unit having a closed chamber, an inlet means for admitting a resuscitation gas into the closed chamber, an outlet means for discharging resuscitation gas to a patient, an exhalation valve which can be selectively opened or closed by a person administering resuscitation gas to a patient for the purpose of selectively discharging gas from the closed chamber to maintaining a predetermined pressure within the chamber, and an insufflation valve associated with the closed chamber to limit the maximum pressure within said chamber.

3 Claims, 1 Drawing Sheet

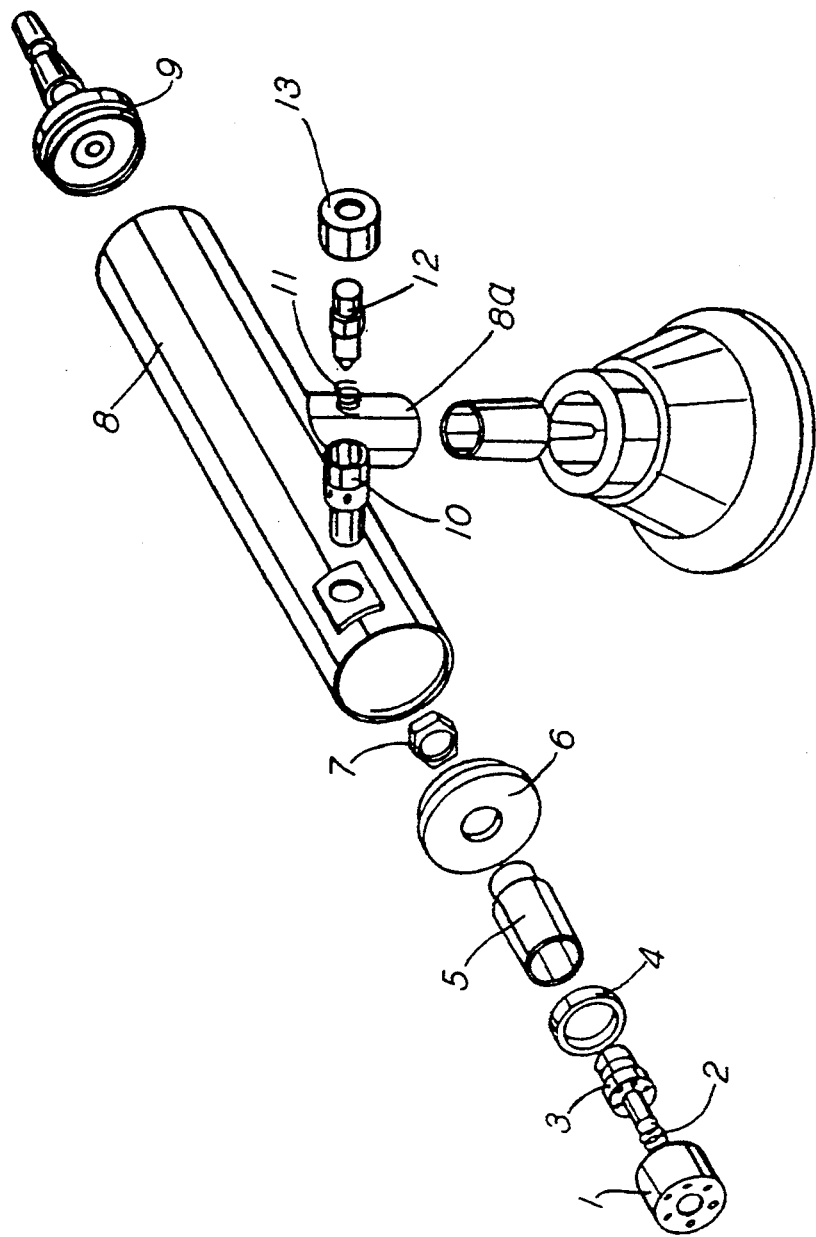

CONTINUOUS-FLOW RESPIRATORY RESUSCITATION UNIT

FIELD OF THE INVENTION

The present invention relates generally to respiratory resuscitation devices, and more particularly to a portable respiratory resuscitation unit which uses a continuous flow of oxygen, either pure or mixed with air, having two valves, one to control the insufflation pressure and one to control the exhalation pressure, each of which can easily be controlled by a single hand holding the device against a patient's face. Accordingly, an attending physician or medic can fully utilize the portable respiratory resuscitation device with one hand, and have the ability to control both the insufflation pressure as well as an exhalation valve, leaving the other hand free to do other things as may be necessary to properly resuscitate a patient.

BACKGROUND OF THE INVENTION

There are several pieces of equipment used for resuscitating purposes which are well known in the medical art. The most commonly used is the AMBU, which consists of a hand piece coupled to a rubber bag, an inlet port for admitting oxygen from a remote source, and a face piece to admit oxygen to the patient. In an AMBU, the oxygen is admitted under pressure to the patient by compressing the rubber bag. While some resuscitating devices are provided with a pressure monitor so that the oxygen pressure admitted to the patient can be monitored, others are provided with a pressure valve so that the oxygen pressure admitted to the patient can be controlled. In most of the AMBUs there is neither a pressure monitor, nor a pressure control valve, so that the oxygen pressure must be "controlled" on the basis of the experience of the physician or medic utilizing the device. It is known, however, that the higher the oxygen pressure, the higher will be the peak inspiratory pressure imposed to the patient, so that a means of controlling the oxygen pressure is highly desirable.

When utilizing these prior art devices, the fraction of oxygen inhaled ($FiO_2$) is not constant, since in most cases the oxygen admitted will be mixed the surrounding, ambient air. Another disadvantage of the prior art devices is that such equipment does not permit control of positive end-expiratory pressure in cases of patients under endotracheal intubation, which can be a serious disadvantage in some cases such as newborn infants, and particularly premature infants.

SUMMARY OF THE INVENTION

This invention is predicated on a new and improve respiratory resuscitation device based on the continuous flow of oxygen, or oxygen mixed with air, which can be handled and fully controlled with one hand. In essence, the improve respiratory resuscitation device is provided with a cylindrical chamber which also functions as a handle, and is provided with three outlet openings in addition to an inlet opening for admitting the resuscitation gas to the cylinder, namely, oxygen or an oxygen-air mixture. One such outlet opening is at the center of the cylinder to which a face piece is attached for admitting the resuscitation gas to the patient, another is provided to which a valve is attached to limit the maximum insufflation pressure, while the third outlet, contains an exhalation valve, which can be occluded.

As will be noted, the respiratory resuscitation device of this invention has a suitable size and shape as necessary so that an adult can handle and use the device with one hand. For proper and effective use, a source of compressed oxygen or oxygen-air mixture is connected to the inlet port with a flexible hose such as a latex hose, preferably through a flowmeter, which is normally affixed on the pressure tank containing the oxygen or oxygen-air mixture. To use the device, the attending physician or medic should determine the desired gas flow rate for the particular patient to be treated. With the patient under endotracheal intubation, and the face mask properly placed on the patient's face, the exhalation valve is occluded by the physician or medic with a simple finger adjustment. The physician or medic will then direct the flow of the resuscitation gas to the patient thereby expanding the pulmonary alveolus up to the level of the pressure limit set by maximum insufflation pressure limiting valve. During this inspiratory time, the proper time limit being determined by the attending physician or medic, the exhalation valve should be occluded to prevent escape of the resuscitation gas. Thereafter, the exhalation phase will commence by opening the exhalation valve, again with a simple finger adjustment, so that the patient can exhale his lungs. A suitable respiratory frequency, as determined by the attending physician or medic, will then be followed. The flow rate should be continued to purge exhaled gases from the mask, and adjusted from time to time, at least three times, during use as may be necessary to prevent or minimize re-inhalation by the patient of exhaled gases.

For use in neonatology and little children, the maximum insufflation pressure limiting valve can be set to a predetermined value corresponding to a selected flow rate (6–7 liters/minute) pursuant to a previously determined scale of pressure to flow rate calculated for use in such applications. This will eliminate the need for a pressure monitor.

BRIEF DESCRIPTION OF THE DRAWING

The invention will be described in detail in connection with the attached drawing, namely FIG. 1, which illustrates an isometric, exploded view of a preferred embodiment of a respiratory resuscitation unit according to this invention.

DETAILED DESCRIPTION OF A PREFERRED EMBODIMENT

The portable respiratory resuscitation device of this invention, as illustrated in FIG. 1, is powered by a continuous-flow of oxygen, either pure or mixed with compressed air, and comprises a cylindrical chamber 8, having a central outlet port 8a, for admitting the resuscitation gas to the patient. The outlet port 8a, has a preferable inner diameter of fifteen millimeters, and a preferable outer diameter of twenty-two millimeters. An inlet port 9 is threaded, or otherwise attached, to one end of cylindrical chamber 8, through which the resuscitation gas is admitted into cylindrical chamber 8. The flow rate of the resuscitation gas will be as set by the flowmeter at the source tank, and admitted by a Latex or plastic hose connecting the tank to the inlet port 9.

Distally to the inlet port 9, there are two valves: the maximum insufflation pressure valve, comprising parts 1, 2, 3, 4, and 5, which is threaded into nut 7, or otherwise attached to cylindrical chamber 8 at end cap 6; and the exhalation valve, comprising parts 10, 11, 12 and 13, attached to the side of cylindrical chamber 8, adjacent to the maximum insufflation pressure valve.

The maximum insufflation pressure valve includes an end cap 1, threaded onto collar 5. A piston 3, having variable diameters, is fitted within sleeve 4. By tightening end cap 1 onto collar 5, compression spring 2 is biased against piston 3. With the increase of resuscitation gas pressure within cylinder 8, piston 3 is moved against the force of spring 2 in proportion to such pressure, so that excess gas is permitted to escape to thereby maintain a constant gas pressure level within cylinder 8. The more end cap 1 is tightened onto collar 5, the more compression spring 2 is compressed against piston 3, so that proportionally greater pressures are required in cylinder 8 to stabilize the gas pressure within cylinder 8. Accordingly, the maximum insufflation pressure, which is the pressure within cylinder 8, can be adjusted by properly adjusting, i.e., tightening end cap 1 onto collar 5.

The exhalation valve includes a valve body 10, which is an open cylinder in shape attached to cylinder 8, and having a base hole (not shown) at the base thereof. A spring 11, is disposed within the cylindrical opening of valve body 10, to be biased against cursor 12. Cursor 12 has a pointed inner end adapted to be fitted into the base hole (not shown) in the base of valve body 10, to close the exhalation valve. A screw cap 13, having a hole in the end through which the outer end of cursor 12 extends, holds cursor 12 against spring 11, such that the exhalation valve is open. The more screw cap 13 is tightened onto valve body 10, the closer cursor 12 is positioned to the base hole (not shown). To completely occlude the exhalation valve, the physician or medic need only to press his or her thumb against cursor 12 extending through the hole in screw cap 13, until it stops against the base hole (not shown), thereby sealing base hole against the escape of any gas within cylinder 8. By releasing such thumb pressure, spring 11 will push cursor 12 from the base hole (not shown), and thereby open the exhalation valve, and permit the gas to be exhausted through the lateral holes in the side of valve body 10. The extent of such pressure drop within cylinder 8, by releasing cursor 12, will depend upon the degree of tightening of screw cap 13 onto cursor 12. The ability to complete occlude the exhalation valve at the end of expiration, and thereby permit a rise of positive pressure of the resuscitation gas within cylinder 8 (due to the continuous inflow), to a limit as set by the maximum insufflation valve, will benefit many patients. The occlusion time of the exhalation valve (inspiratory time), as well as the exhalation time during which the exhalation valve is open, must be determined by the attending physician or medic for each patient. The attending physician or medic should also set the gas flow rate to avoid re-inhalation of expired gas, which setting should be at least three times the patient's inhalation rate.

It is believed that the above described respiratory resuscitation unit will significantly improve the ability to treat patients, particularly those in risk of loss of life, since the device:

1. permits the constant flow of resuscitation gas, including up to 100% pure oxygen;
2. permits the setting of a maximum insufflation pressure;
3. permits the onset of a positive pressure at the end of expiration;
4. permits a continuous positive pressure during insufflation;
5. permits coupling to a pressure monitor;
6. permits operation with a minimum effort by the attending physician of medic; and
7. permits the elimination or reduction of re-inhalation of exhaled gases.

As should be apparent, the device can be used in intensive care units, nurseries, transportation of patients in need of ventilation support, emergency units, anesthesiology and other such locations where ventilation support of a patient is necessary.

I claim:

1. A continuous-flow respiratory resuscitation unit comprising; a body structure defining a closed chamber, said body having means permitting said unit to be easily held and utilized with one hand, said body structure further including:
   (a) inlet means for continuously admitting a resuscitation gas into said chamber,
   (b) outlet means having a face piece thereon said outlet means discharging such resuscitation gas within said chamber to a patient,
   (c) an exhalation valve having means for selectively opening and closing said exhalation valve by a person administering such resuscitation gas to such a patient for the purpose of selectively discharging gas from said chamber, and
   (d) an adjustable insufflation valve having means for selectively controlling the maximum pressure within said chamber.

2. A continuous-flow respiratory resuscitation unit according to claim 1 in which said chamber is small enough to be held with one hand, and said exhalation valve further comprises means for operating said exhalation valve by one or more fingers of a hand holding said chamber.

3. A continuous-flow respiratory resuscitation unit according to claim 1 or 2 in which said chamber further comprises means for receiving a continuous flow oxygen, thereby permitting the resuscitation of a patient with oxygen in concentrations up to 100%, in a suitable flow which prevents re-inhalation of gases.

* * * * *